(12) United States Patent
Ratjen

(10) Patent No.: US 8,062,268 B2
(45) Date of Patent: Nov. 22, 2011

(54) INJECTOR WITH THUMB OPERABLE SCROLL WHEEL

(75) Inventor: Jochen Ratjen, Nacka (SE)

(73) Assignee: SHL Group AB, Nacka Strand (SE)

( * ) Notice: Subject to any disclaimer, the term of this patent is extended or adjusted under 35 U.S.C. 154(b) by 0 days.

(21) Appl. No.: 12/864,036

(22) PCT Filed: Dec. 4, 2008

(86) PCT No.: PCT/EP2008/066746
§ 371 (c)(1),
(2), (4) Date: Aug. 14, 2010

(87) PCT Pub. No.: WO2009/095129
PCT Pub. Date: Aug. 6, 2009

(65) Prior Publication Data
US 2010/0305501 A1    Dec. 2, 2010

(30) Foreign Application Priority Data

Jan. 28, 2008   (SE) ........................... 0800207

(51) Int. Cl.
*A61M 5/19* (2006.01)
(52) U.S. Cl. ..................................... 604/224

(58) Field of Classification Search ............... 604/82, 604/181, 187, 218, 224
See application file for complete search history.

(56) References Cited

U.S. PATENT DOCUMENTS

| 2,644,450 | A * | 7/1953 | Krewson | 604/181 |
| 6,648,850 | B2 * | 11/2003 | Landau | 604/70 |
| 7,402,150 | B2 * | 7/2008 | Matsumoto et al. | 604/90 |
| 2002/0173752 | A1 * | 11/2002 | Polzin | 604/233 |
| 2008/0045971 | A1 * | 2/2008 | Ayton et al. | 606/107 |
| 2008/0114305 | A1 * | 5/2008 | Gerondale | 604/207 |
| 2008/0255525 | A1 * | 10/2008 | Taufig | 604/207 |

* cited by examiner

*Primary Examiner* — Nicholas Lucchesi
*Assistant Examiner* — Aarti B Berdichevsky
(74) *Attorney, Agent, or Firm* — Potomac Patent Group PLLC

(57) ABSTRACT

The present invention relates to an injector comprising a housing (10); a medicament container (12) disposed within the housing, wherein the container has at least one chamber, a front opening with or for an injection needle for delivering the medicament therethrough, and at least one movable stopper; a drive unit (22) slidable arranged within the housing, and capable of acting on said container for expelling medicament through said needle; and a scroll wheel member (24) operatively connected to said housing via a transmission and wherein said scroll wheel member comprises friction enhancing means such that it is capable of being maneuverable with a finger of a user for performing a function.

7 Claims, 3 Drawing Sheets compression spring

INJECTOR WITH THUMB OPERABLE SCROLL WHEEL

TECHNICAL AREA

The present invention relates to an injector for performing a function as injecting or mixing a medicament and in particular an injector which is very simple to use also for patients with weak hands or reduced manual dexterity.

TECHNICAL BACKGROUND

Many injectors have been developed during the years with different degrees of functions such as automatic penetration and/or injection, setting of different doses to be injected, retractable and lockable needle shields, means for performing mixing and priming, to mention a few.

Automatic functions may have their advantages in that they reduce the actions that the user needs to perform. On the other hand an increased degree of automation and/or number of functions by necessity entails an increased number of components that need to interact with each other in reliable and repeatable ways without the risk of malfunction or breakdown of the device, which otherwise could jeopardize the health of the patient. Further, the increased number of components also increases the cost of the device.

For most injectors, and for most patients, a number of actions of the injector may be performed manually, such as penetration and/or injection. However, for many drugs and administering schemes it is an advantage that the dose to be delivered may be set before injection.

One such injector is disclosed in patent application No. WO 0110484. It describes an injector having a dose setting means whereby the rear end of the injector is turned until the desired dose is displayed. The turning causes the rear part of the injector to protrude more and more out of the housing of the injector due to threads between the rear part and the housing. When the patient is to inject the medicament, he/she presses on the protruding part, whereby it is pushed back into the housing. This movement causes the protruding part to rotate back during injection.

For most patients, the force required to perform the injection is manageable where the force depends inter alia on the pitch of the threads, the resistance of the stopper inside the medicament container and the diameter of the needle channel. In that respect there is an increased demand from patients to use as small needles as possible in order to reduce the pain induced by the penetrating needle.

However, for patients/users with weak hands and fingers, with reduced manual dexterity, the force required for the injection is too high, so that they cannot operate the injector. The problem becomes more severe the longer the rear part is rotated out of the housing. Also for patients that self-inject on places on the body where they cannot see, such as in the buttock or the rear waist, having a push button on the rear of the injector is not optimal.

There is thus a demand for an injector having manual injection features that can be handled in an easy and reliable way also by patients with reduced manual dexterity as well as when the injector is held in positions where pushing on the rear end of the injector is not optimal.

BRIEF DESCRIPTION OF THE INVENTION

The aim of the present invention is to remedy the above mentioned problems with the present injectors. This aim is obtained according to the present invention with an injector comprising the features of the independent patent claim 1.

Preferable embodiments of the present invention form the subject of the dependent patent claims.

According to a main aspect of the present invention, it is characterised by an injector comprising a housing; a medicament container disposed within the housing, wherein the container has at least one chamber, a front opening with or for an injection needle for delivering the medicament therethrough, and at least one movable stopper; a drive unit slidable arranged within the housing, and capable of acting on said container for expelling medicament through said needle; and a scroll wheel member operatively connected to said housing via a transmission and wherein said scroll wheel member comprises friction enhancing means such that it is capable of being maneuverable with a finger of a user for performing a function.

According to another aspect of the present invention said transmission comprises at least one cog wheel and a toothed rack on said housing, such that said at least one cog wheel is capable of acting on the toothed rack when said scroll wheel member is operated.

According to a further aspect of the present invention, said function comprises an injection of a medicament, or a penetration and an injection, or a mixing of a medicament.

The advantages with the present invention are several. The use of a scroll wheel member provides a completely new approach to handling injectors for performing different functions as penetrating and/or injecting, or mixing. Traditionally most injectors are maneuvered by pressing the rear part of the injector when injecting a medicament or by screwing two parts when mixing a medicament. With the scroll wheel member, it may be placed on many places on the injector depending on the intended use. Further, with the scroll wheel member, it is very simple to combine this with a transmission, which in turn enables the use of very low forces in order to handle the injector, which is a great advantage for users with weak hands, like children or elderly people with rheumatism, but also generally for persons with reduced manual dexterity.

The scroll wheel member also enables a very smooth and precise control of the injection, which is an advantage when injecting medicament that expands inside the tissue or is somewhat painful to inject. Then the patient can control the speed of the injection in a precise way with the scroll wheel member.

The transmission may be performed in several ways that provide different advantages and solutions and in particular enables a flexible positioning of the scroll wheel member. Thus for some applications and injection sites, it is an advantage that the scroll wheel member is placed in the rear of the injector, such as when penetrating the stomach, as with insulin, or the front side of the thigh.

For other applications it is an advantage when the scroll wheel member is placed in the front of the injector, such as when penetrating the buttock or rear part of the waist or the underside of the upper arm.

Apart from handling the function of injecting, it is readily apparent to the person skilled in the art, when presented with the present invention, that the scroll wheel member also could handle a penetration movement if the injector is arranged with a slidable medicament cartridge or container. Further, the person skilled in the art understands that the injector according to the present invention could be arranged with dose setting means, which controls the amount the scroll wheel can be rotated in order to deliver a preset specific quantity of medicament.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

The present invention relates to an injector comprising a housing; a medicament container 12 disposed within the housing, wherein the container has at least one chamber, a front opening with or for an injection needle for delivering the medicament therethrough, and at least one movable stopper; a drive unit 22 slidable arranged within the housing, and capable of acting on said container for expelling medicament through said needle; and a scroll wheel member 24 operatively connected to said housing via a transmission and wherein said scroll wheel member comprises friction enhancing means such that it is capable of being maneuverable with a finger of a user for performing a function.

Figure 1:
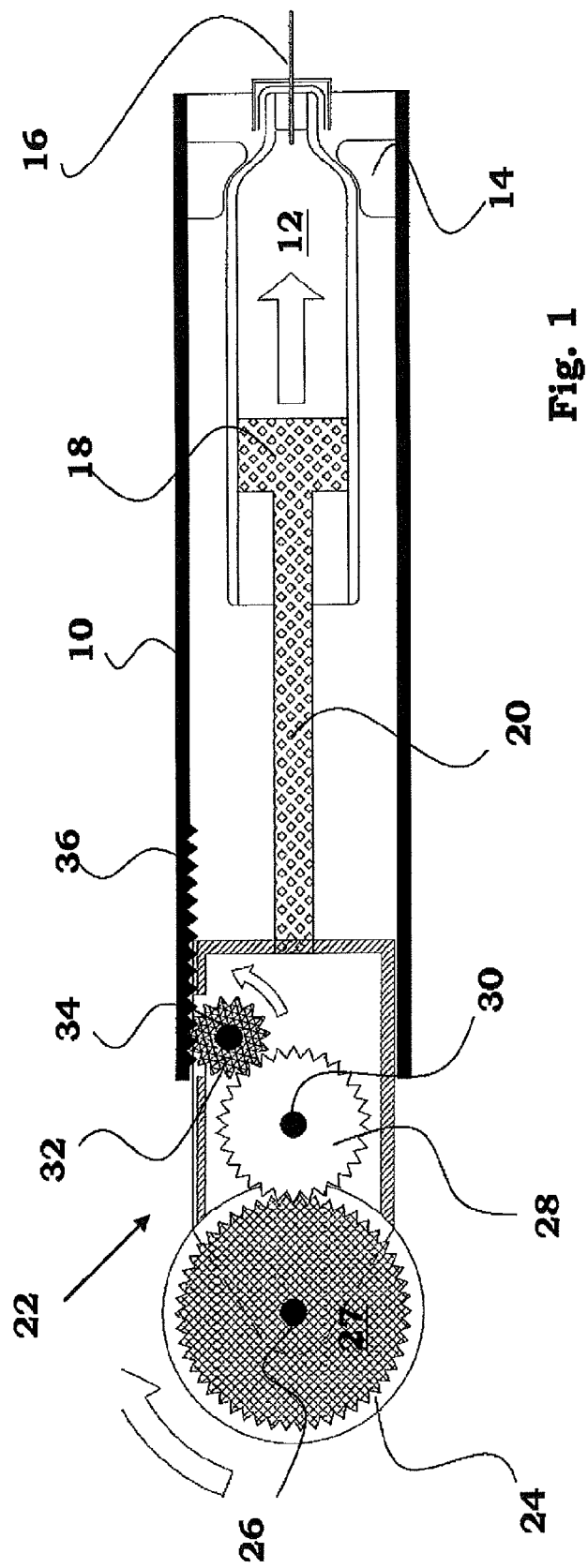
FIG. 1 shows a first embodiment of the invention in a cross-sectional view.
Figure 2:
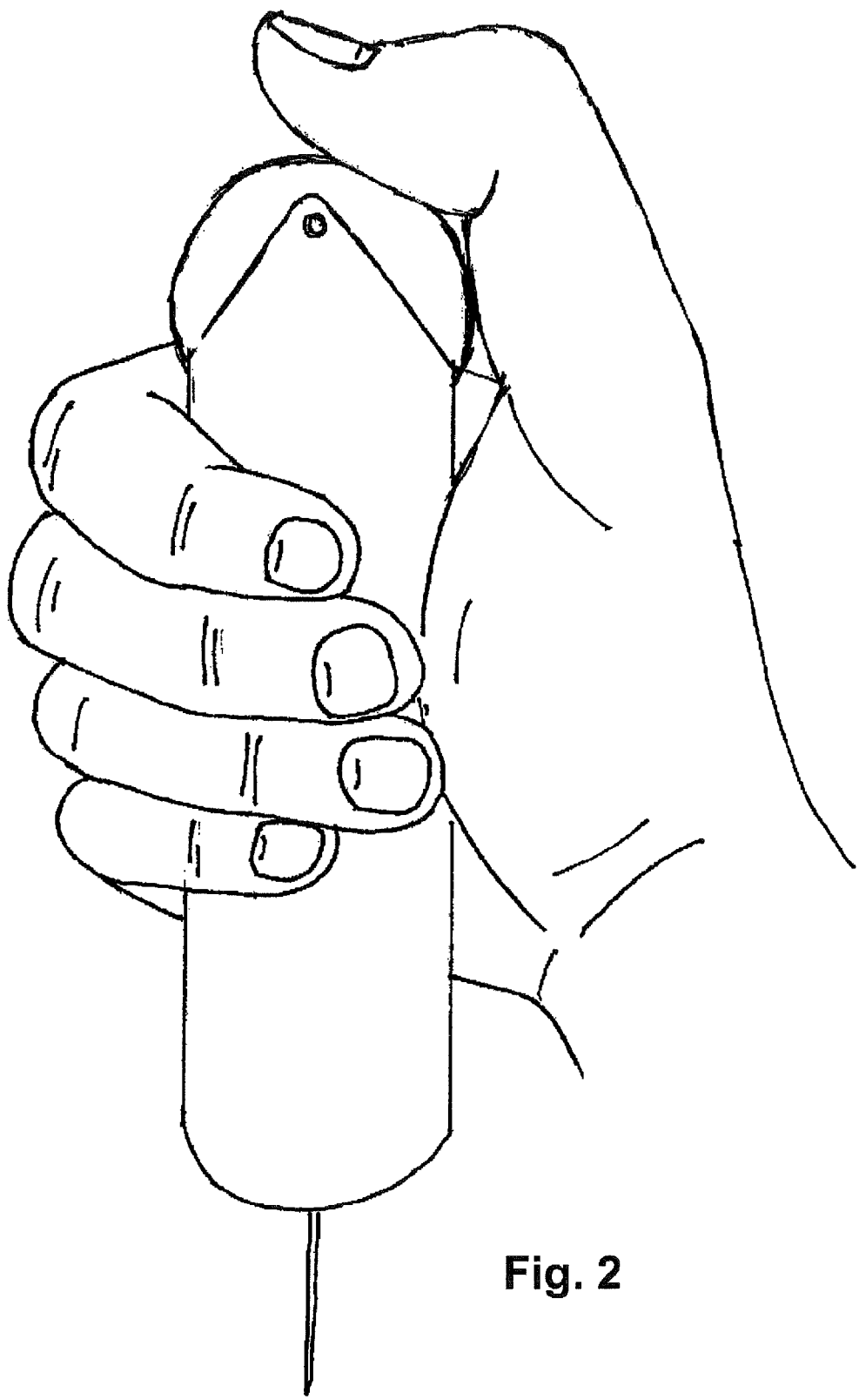
FIG. 2 shows a preferred grip of the injector according to FIG. 1.

In the embodiment shown in FIG. 1, the medicament container 12 is placed inside a housing 10 and held in position by supports 14. An injection needle 16 is attached to the front end of the container, where the needle protrudes somewhat out of the housing. A needle cover or cap (not shown) may be releasably attached to the front end of the housing, surrounding the needle as protection from the needle when the injector is not used. Inside the container a stopper 18 is arranged to be slidable in order to expel medicament through the needle channel.

The drive unit comprises a plunger rod 20 which is in contact with its front end with the stopper. In the embodiment shown in FIG. 1, the rear end of the drive unit is of a generally tubular shape having a diameter somewhat smaller than the inner diameter of the housing, whereby the drive unit is slidable arranged inside the housing, and wherein the rear end protrudes somewhat out of the rear end of the housing.

The scroll wheel member 24 is rotatable attached to the drive unit 22 around an axis 26, which is generally perpendicular to the longitudinal axis of the injector. The scroll wheel member has a diameter such that at least part of its circumference protrudes outside the drive unit thus accessible by a finger of a user, preferably the thumb, when the injector is gripped. The scroll wheel member comprises thereby friction enhancing means around its circumference surface, such as rubber, grooves, dimples and the like.

The transmission comprises at least one cog wheel and a toothed rack 36. Said toothed rack 36 being arranged on said housing, such that said at least one cog wheel is capable of acting on the toothed rack 36 when the scroll wheel member is operated.

In the embodiment shown in FIG. 1, the scroll wheel member is attached to a first cog wheel 27 which in turn meshes with a second cog wheel 28 rotatable around an axis 30. The second cog wheel meshes with a third cog wheel 32 rotatable around an axis 34, and which third cog wheel meshes with a toothed rack 36 arranged on the inner surface of the housing 10.

The injector of the embodiment shown in FIG. 1 is intended to function as follows. When the patient is to perform the function of injecting a medicament, the protective cap is removed. The injector should now be held in a firm grip with all fingers but the thumb surrounding the housing, and with the thumb resting on the scroll wheel member 24 at the rear of the injector, as seen in FIG. 3. The needle then penetrates the injection site by the user pushing the injector manually. When the needle has penetrated to the right depth, which is when the front end of the housing is in contact with the injection site, the user then operates the scroll wheel member with the thumb. The scroll wheel member is thus rotated by the thumb acting on its circumference. This rotation is then transmitted through the transmission whereby the drive unit 22 is linearly moved into the housing. The movement of the drive unit in turn causes the plunger rod 20 to move, whereby the stopper 18 is also moved and medicament is expelled through the needle 16.

When the injection is completed, the needle is withdrawn from the injection site and the protective cap is put back on the injector, covering the needle.

Figures 3A, 3B, 3C:
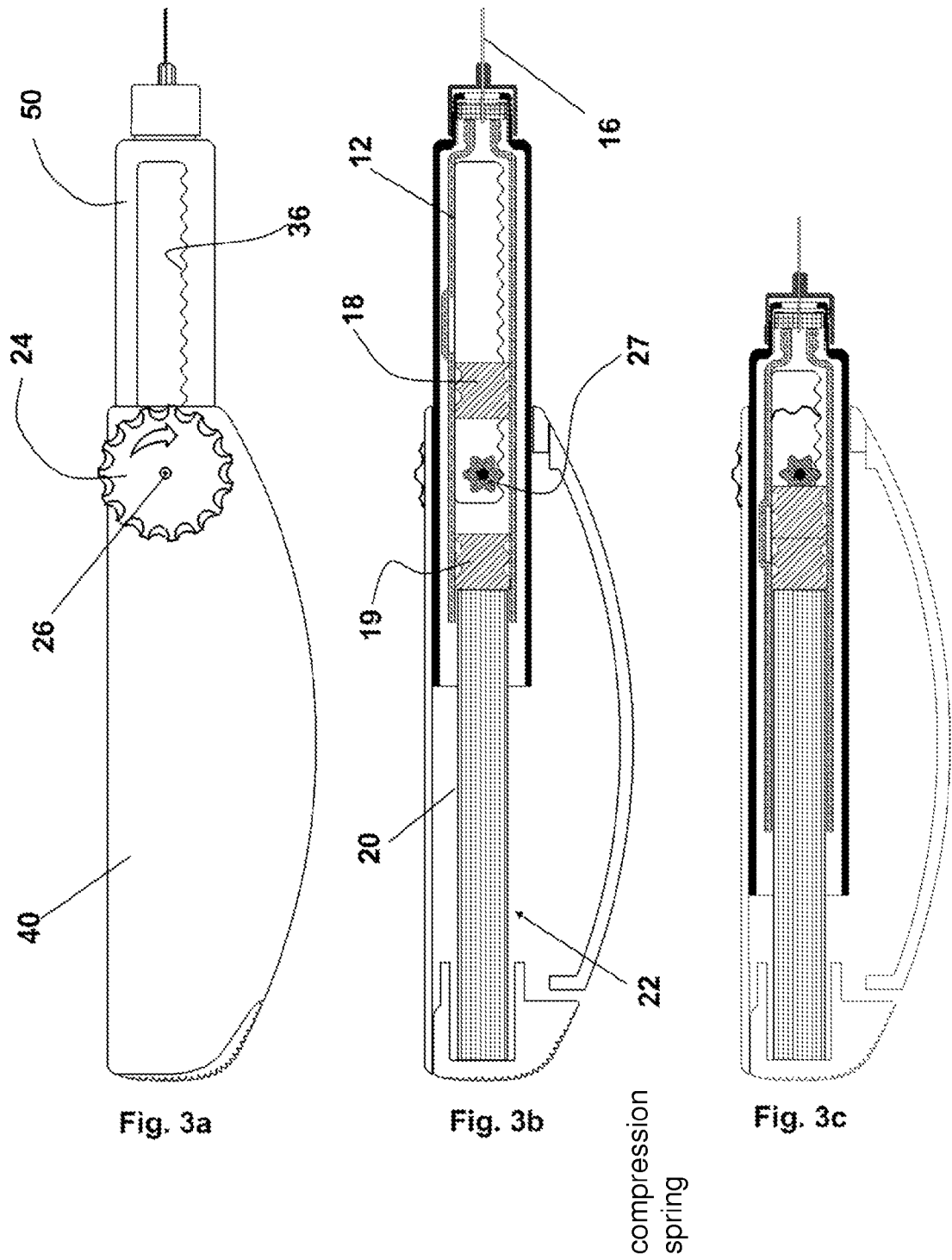
FIG. 3a shows a second embodiment of the invention.
FIG. 3b shows a cross-sectional side view of the injector according to FIG. 3a in a medicament pre-mixed position.
FIG. 3c shows a cross-sectional side view of the injector according to FIG. 3a in a medicament mixed position.

FIGS. 3a-c show a second embodiment of the present invention. In the second embodiment, the housing comprises a rear housing 40 and a front housing 50, wherein said front housing is arranged to be slidable inside said rear housing. The medicament container 12 is placed inside the front housing and an injection needle 16 is attached to the front end of the container. A needle cover or cap (not shown) may be releasably attached to the front end of the housing, surrounding the needle as protection from the needle when the injector is not used. The container comprises a first chamber containing a first agent and a second chamber containing a second agent. These chambers are sealed off with stoppers in order that the agents do not become degraded. When the agents are to be mixed shortly before injection, redirecting passages of the container are opened between the chambers, usually by moving a rear stopper 19 and in turn a divider stopper 18 of the container somewhat. The passages allow the mixing of the medicament agent and the diluent and the medicament is ready for delivery. The drive unit 22 is still slidable inside the housing and comprises a plunger rod connected to a power source such as a compression spring for urging the plunger rod against the stopper for expelling medicament through the injection needle.

The transmission comprises at least one cog wheel 27 and a toothed rack 36. Said toothed rack 36 being arranged on said front housing 50, such that said at least one cog wheel is capable of acting on the toothed rack 36 when said scroll wheel member is operated.

In the second embodiment, the scroll wheel member 24 is rotatable attached to the rear housing 40 around an axis 26, which is generally perpendicular to the longitudinal axis of the injector. The scroll wheel member comprises friction enhancing means around its circumference surface, such as rubber, grooves, dimples and the like. The scroll wheel member is attached to said at least one cog wheel 27 which in turn meshes with said toothed rack 36 arranged on the surface of the front housing 50.

The injector of the second embodiment is intended to function as follows. When the patient is to perform the function of mixing a medicament, the user operates the scroll wheel member by rotating it with his/her thumb. This rotation is then transmitted through the transmission whereby the front housing is linearly moved into the rear housing. The movement of the front housing in turn causes the rear stopper 19 which rest against the front end of the plunger rod and the divider stopper to move inside the container, whereby the agents inside said container mixes completely.

In the embodiment shown in FIG. 1, the scroll wheel member is used for performing the function of injecting a medicament, but it is to be understood that also the penetration may be performed by the action of the scroll wheel member, whereby the injector may be modified slightly so that the container is arranged slidable inside the housing.

Further, the injector may be arranged with dose setting means such that the scroll wheel member may only be rotated a certain amount, corresponding to a certain preset dose volume. In that respect, the scroll wheel member may be arranged with indications regarding dose size.

The scroll wheel member or the transmission may further be arranged with audio and/or tactile means that indicates when the scroll wheel member is rotated. The scroll wheel member or the transmission may further be arranged with some sort of rotational lock preventing the scroll wheel member to be rotated in the wrong direction. There may further be a safety lock connected to the scroll wheel member or the transmission, thereby avoiding unintentional activation of the injector by rotating the scroll wheel member.

It is to be understood that the embodiments described above and shown in the drawings are to be regarded only as non-limiting examples of the invention and that it may be modified in many ways within the scope of the patent claims.

The invention claimed is:

1. An injector, comprising:
    a housing, comprising a rear housing and a front housing, wherein the front housing is slidably arranged inside the rear housing;
    a medicament container, being disposed inside the front housing and comprising a first chamber containing a first agent, a second chamber containing a second agent, a rear stopper, and a divider stopper;
    a front opening configured for an injection needle for delivering the medicament therethrough;
    a drive unit slidably arranged within the housing and configured to act on the container for expelling medicament through the needle; and
    a scroll wheel member attached to the rear housing and rotatable around an axis generally perpendicular to a longitudinal axis of the injector, wherein the scroll wheel member is operatively connected to the front housing via a transmission and the scroll wheel member comprises a friction enhancing device such that the scroll wheel member is maneuverable with a finger of a user for mixing a medicament.

2. The injector of claim 1, wherein the drive unit comprises a plunger rod connected to a power source for urging the plunger rod against the stopper for expelling medicament through the needle.

3. The injector of claim 2, wherein the power source is a compression spring.

4. The injector of claim 1, wherein the transmission comprises at least one cog wheel and a toothed rack on the front housing, and the at least one cog wheel is configured to act on the toothed rack when the scroll wheel member is operated.

5. The injector of claim 1, wherein the scroll wheel member linearly moves the front housing to the rear housing.

6. The injector of claim 5, wherein the drive unit comprises a plunger rod connected to a compression spring for urging the plunger rod against the stopper for expelling medicament through the needle.

7. The injector of claim 5, wherein the transmission comprises at least one cog wheel and a toothed rack on the front housing, and the at least one cog wheel is configured to act on the toothed rack when the scroll wheel member is operated.

* * * * *